United States Patent
Cannara et al.

(10) Patent No.: US 10,960,456 B2
(45) Date of Patent: *Mar. 30, 2021

(54) PROGRAMMABLE MOTOR DRIVEN SWAGING PRESSES FOR ATTACHING SURGICAL NEEDLES TO SUTURES

(71) Applicant: Ethicon, Inc., Somerville, NJ (US)

(72) Inventors: Alexander M. Cannara, Roseland, NJ (US); Frank Richard Cichocki, Jr., Easton, PA (US)

(73) Assignee: Ethicon, Inc., Somerville, NJ (US)

( * ) Notice: Subject to any disclaimer, the term of this patent is extended or adjusted under 35 U.S.C. 154(b) by 703 days.

This patent is subject to a terminal disclaimer.

(21) Appl. No.: 15/465,893

(22) Filed: Mar. 22, 2017

(65) Prior Publication Data

US 2018/0272416 A1     Sep. 27, 2018

(51) Int. Cl.
*B21J 9/20*     (2006.01)
*B21G 1/08*     (2006.01)
(Continued)

(52) U.S. Cl.
CPC ........... *B21J 9/20* (2013.01); *A61B 17/06004* (2013.01); *A61B 17/06066* (2013.01);
(Continued)

(58) Field of Classification Search
CPC ......... A61B 17/06004; B21J 9/06; B21J 9/20; B21D 39/048
See application file for complete search history.

(56) References Cited

U.S. PATENT DOCUMENTS 3,842,651 A * 10/1974 Shaffer ............... B21J 9/06
                                                     72/451
3,875,946 A    4/1975 Duncan
(Continued)

FOREIGN PATENT DOCUMENTS

| CA | 1022734 | 12/1977 |
| EP | 0663187 | 7/1995 |

(Continued)

OTHER PUBLICATIONS

Janome: "Janome Industrial Equipment USA,Inc. Home", Mar. 8, 2017 (Mar. 8, 2017), XP055466470, janomeie.com Retrieved from the Internet: URL:http://web.archive.org/web/20170308080728/http://www.janomeie.com:80/products/electro press/jps series/spec.html [retrieved on Apr. 11, 2018], p. 3.

(Continued)

*Primary Examiner* — Moshe Wilensky
*Assistant Examiner* — Kyle A Cook

(57) ABSTRACT

A swaging system for attaching surgical needles to sutures and testing the attachment strength includes a frame, a bottom swaging die mounted on the frame, and a top swaging die mounted on the frame and being moveable up and down along a swaging axis that is aligned with the bottom swaging die. The bottom swaging die includes a hinge mechanism with a bottom plate mounted to the frame and a top plate overlying the bottom plate. The top and bottom plates are pivotally connected for enabling the top plate to pivot relative to the bottom plate. The bottom swaging die includes a swaging tool that extends toward the top swaging die along the swaging axis, and a load cell disposed between the top and bottom plates for monitoring load. The system includes a control system having one or more pull test programs stored therein for conducting pull (Continued)

tests on armed surgical needles to determine if the armed surgical needles are acceptable or unacceptable.

21 Claims, 9 Drawing Sheets

(51) Int. Cl.
  *B21J 9/06* (2006.01)
  *A61B 17/06* (2006.01)
  *B21D 39/04* (2006.01)
  *A61B 17/00* (2006.01)
(52) U.S. Cl.
  CPC ............. *B21D 39/048* (2013.01); *B21G 1/08* (2013.01); *B21J 9/06* (2013.01); *A61B 2017/00526* (2013.01); *A61B 2017/00946* (2013.01); *A61B 2017/06028* (2013.01)

(56) References Cited

U.S. PATENT DOCUMENTS

| | | |
|---|---|---|
| 3,890,975 A | 6/1975 | McGregor |
| 3,980,177 A | 9/1976 | McGregor |
| 4,060,885 A | 12/1977 | Hoffman et al. |
| 4,613,800 A | 9/1986 | Jeppsson |
| 4,939,918 A * | 7/1990 | Schoch ................ B21D 51/383 72/19.9 |
| 5,092,026 A | 3/1992 | Klemmer et al. |
| 5,230,352 A | 7/1993 | Putnam et al. |
| 5,383,902 A | 1/1995 | Carpentiere et al. |
| 5,394,971 A | 3/1995 | Colligan et al. |
| 5,438,746 A | 8/1995 | Demarest et al. |
| 5,487,216 A | 1/1996 | Demarest et al. |
| 5,500,991 A | 3/1996 | Demarest et al. |
| 5,623,189 A | 4/1997 | Hemmer |
| 5,707,391 A | 1/1998 | Carpentieri et al. |
| 5,793,634 A * | 8/1998 | Demarest ................ G05B 19/18 29/705 |
| 5,844,142 A | 12/1998 | Blanch et al. |
| 5,903,966 A | 5/1999 | Sonderegger |
| 5,942,765 A | 5/1999 | Shikakubo et al. |
| 5,918,284 A | 6/1999 | Blanch et al. |
| 5,920,482 A | 7/1999 | Demarest et al. |
| 5,948,997 A | 9/1999 | Schmidt |
| 6,016,682 A | 1/2000 | Tannhauser et al. |
| 6,058,821 A | 5/2000 | Demarest et al. |
| 6,081,981 A | 7/2000 | Demarest et al. |
| 6,163,948 A | 12/2000 | Esteves et al. |
| 6,647,803 B1 | 11/2003 | Demarest et al. |
| 6,845,645 B2 | 1/2005 | Bartrom et al. |
| 6,877,352 B1 * | 4/2005 | Schlereth ......... A61B 17/06004 29/282 |
| 7,185,411 B2 | 3/2007 | Lenihan et al. |
| 8,214,996 B2 | 7/2012 | Stametz et al. |
| 2005/0166384 A1 | 8/2005 | Lenihan et al. |
| 2008/0034985 A1 * | 2/2008 | Suzuki ..................... B30B 1/14 100/35 |
| 2008/0119876 A1 | 5/2008 | Price et al. |
| 2009/0158577 A1 * | 6/2009 | Schweikle ............ B23P 21/002 29/428 |
| 2018/0272416 A1 | 9/2018 | Cannara et al. |

FOREIGN PATENT DOCUMENTS

| | | |
|---|---|---|
| EP | 0875207 | 11/1998 |
| JP | 3024773 | 3/2000 |
| JP | 2013081885 | 5/2013 |

OTHER PUBLICATIONS

Janome: "Janome JP-S Series—New Generation Servo Press", Sep. 9, 2016 (Sep. 9, 2016), XP055466520, Retrieved from the Internet: URL:http://temas.vn/Uploads/documents/Unipulse/Servo%20press%20JP-S.pdf.pdf [retrieved on Apr. 11, 2018].

International Search Report issued in corresponding International Application No. PCT/US2018/017551, dated Apr. 24, 2018, 5 pages.

International Search Report issued in International Application No. PCT/US2018/017560, dated Apr. 30, 2018, 5 pages.

SMAC Moving Coil Actuators, SMAC Corporation of Carlsbad, California, www.smac-mca.com/technical-resources/moving-coil-technology, 2017, 2 pages.

\* cited by examiner

PROGRAMMABLE MOTOR DRIVEN SWAGING PRESSES FOR ATTACHING SURGICAL NEEDLES TO SUTURES

BACKGROUND OF THE INVENTION

Field of the Invention

The present patent application is generally related to attaching surgical needles to sutures, and is more particularly related to swaging presses used for attaching surgical needles to sutures.

Description of the Related Art

Armed surgical needles, i.e., needles having sutures attached to one end thereof, are typically manufactured utilizing manual, semi-automated, or fully automated procedures whereby a length of suture material is inserted into a suture receiving opening of a surgical needle, and the needle is swaged (i.e., compressed) to attach the surgical needle to the end of the suture.

Swaging of suture needles typically involves inserting the free end of a suture into an axial bore of a needle barrel, and holding the suture inside the axial bore while a swage die impinges upon the outer surface of the needle barrel, thereby compressing a portion of the bore onto the suture. The compressed portion of the axial bore grasps the suture by mechanical interference and by surface friction. The swaging process is conducted to create an attachment between the needle barrel and the suture that meets or exceeds "pull-out" strength standards.

FIG. 1 illustrates a prior art method of swaging a needle N to a suture S utilizing a single-sided, multiple indentation swaging protocol. The suture S is inserted into a suture receptacle SR of the needle N, and at least one stake point of a die is driven into one side of the needle N to deform the wall W of the needle and create a depression $D_1$ that causes the wall W to impinge upon the suture S, creating a pressure point $P_1$ between the depression $D_1$ and the opposing portion of the needle wall W. One or more additional indentations $D_2$ can be made to create additional pressure points, e.g. $P_2$. The suture S is retained in the needle N by virtue of the impingement of a small portion of the needle wall W on a correspondingly limited area of the suture S.

FIG. 2 illustrates another prior art method of swaging a needle N to a suture S utilizing a double-sided, aligned swaging protocol. The suture S is inserted within a suture receptacle SR of a needle N, and two opposing stakes are utilized to create aligned depressions $D_3$, $D_4$ that form a pressure point $P_3$ between the two depressions, $D_3$, $D_4$ for grasping the suture S. The focused pressure at $P_3$ may create sheer stress that could result in fracturing of the suture S, leading to suture detachment. To avoid exceeding the sheer stress limits of the suture material, the dimensions of the suture receptacle SR, the thickness and deformability of the wall W of the needle N, and the depression depth of the depressions $D_3$ and $D_4$ are controlled.

FIG. 3 shows a prior art needle swaging assembly 20 with first and second swage dies 22A, 22B converging to hold a needle N for swaging. The needle N is gripped between needle holders 24A, 24B and abuts against needle stops 26A, 26B with the suture receptacle SR aligned with the suture grooves 28A, 28B. Insertion of the needle N between the needle holders 24A, 24B is facilitated by needle funnel portions 30A, 30B. A suture funnel 32 aides in threading the suture S through the suture grooves 28A, 28B and into the suture receptacle SR of the needle N. Swaging elements 34A, 34B are free to slide within respective slots 36A, 36B so that the stakes 38A, 38B thereof can impinge upon the needle N. In the embodiment shown in FIG. 3, the stakes 38A are laterally offset relative to the stakes 38B such that when the swaging elements 34A, 34B are urged together during the swaging operation, the needle N will be swaged to create a serpentine configuration in the suture receptacle SR. A greater or lesser number of stakes 38A, 38B may be utilized, ranging from one stake 38A, 38B on each swaging element 34A, 34B, up to any selected number of stakes 38A, 38B. The height, spacing and shape of the stakes 38A, 38B, as well as the relative lateral offset of the stakes 38A, 38B on opposite swaging elements 34A, 34B may be selected to adjust swaging and suture attachment strength.

One approach to providing good suture attachment uses a multiple hit swaging process, whereby a needle is subjected to swaging of a controlled depth, however, the compression is distributed over a large area of the needle barrel (e.g., around the circumference of the needle barrel). To achieve this type of swaging, the needle may be rotated relative to the swaging dies between multiple swaging events. In this manner, multiple angularly offset swaging events are performed to attach a single needle to a single suture. While this approach provides a reliable attachment, each hit on the barrel of the needle produces stress in the needle barrel and the suture. The needle and suture materials have some degree of malleability, but when the limit of malleability is reached (e.g., too much displacement or force applied to the needle barrel), the materials will fail, leading to, in the case of the needle, cracking and loss of attachment, or breakage. Cracking is a particular problem when harder alloys are used, including advanced alloys such as 4310 SS, nickel-titanium SS, and 420 SS. Further, needle materials have some elasticity, such that the relief of residual stress causes the needle barrel to relax over time, leading to a loss of attachment between the needle bore and the suture.

Existing swaging presses are based on either pneumatic or simple mechanical linkages that are actuated to conduct relatively simple motions that are limited by the mechanical design of the press. Some of the shortcomings exhibited by existing swaging presses include 1) difficulty in making set-up adjustments, 2) the inability to measure the force applied to the suture needle during swaging and precisely control swage die displacement based on real time force feedback, 3) the inability to measure location (or displacement) of the swaging dies and provide real time feedback on the location, 4) the inability to apply multiple percussive strikes during a single swaging stroke, 5) the inability to pause and hold a force during needle swaging before continuing the cycle to a higher force level, 6) the inability to send the operator an alarm when the force or displacement values are detected to be out of a predetermined range, which is especially important to prevent needle barrel cracking when the needle is incorrectly placed in the receiving die, 7) the inability to gather a force-displacement curve during swaging and provide an accept/reject signal to the swaging operator based on an analysis of the force-displacement curve, 8) the inability to control and change the rate of die displacement or force accumulation during the swaging event according to a pre-programmed algorithm, and 9) the inability to automatically tare the press displacement to insure an easy and repeatable set up procedure.

Therefore, there remains a need for swaging presses designed to overcome the above limitations in order to improve needle pull off values associated with fine size sutures used in cardiovascular surgery. There also remains a need for improved swaging presses that utilize servomotors, load cells, sensors, programs, and real time feedback protocols to make armed surgical needles in more efficient, effective, and reliable ways. In addition, there remains a need for improved swaging presses that use fine needles and suture materials to make armed surgical needles for delicate surgical procedures.

SUMMARY OF THE INVENTION

In one embodiment, a programmable swaging press for attaching surgical needles to sutures preferably includes a bottom swaging die, and a top swaging die opposing the bottom swaging die and being moveable up and down along a swaging axis that is aligned with the bottom swaging die. In one embodiment, a load cell is provided on the bottom swaging die for recording load data, and a servomotor is coupled with the top swaging die for recording location data that corresponds to the location of the top swaging die on the swaging axis. In one embodiment, the programmable swaging press desirably includes a control system having a microprocessor in communication with the load cell and the servomotor. In one embodiment, the microprocessor uses the recorded load data to determine the total load applied during a swage event, and the microprocessor uses the recorded location data to calculate the total displacement during the swage event.

In one embodiment, the bottom swaging die desirably includes a hinged mechanism with a bottom plate and a top plate that overlies the bottom plate. In one embodiment, the top and bottom plates are pivotally connected to one another for enabling the top plate to pivot relative to the bottom plate. In one embodiment, the load cell is disposed between the top and bottom plates and is adapted to send the recorded load data to the microprocessor.

In one embodiment, the programmable swaging press desirably has a frame, a guide rail secured to the frame, and a precision slide coupled with the guide rail for moving between upper and lower ends of the guide rail, whereby the top swaging die is mounted on the precision slide. In one embodiment, the servomotor is coupled with the precision slide for controlling up and down movement of the precision slide between the upper and lower ends of the guide rail, which, in turn, controls up and down movement of the top swaging die along the swaging axis.

In one embodiment, the control system preferably has one or more swage programs stored therein for forming armed surgical needles. In one embodiment, each swage program has a displacement limit and a load limit for use during a swage event. Each program may be associated with a needle and a suture having particular sizes or properties. In one embodiment, the displacement, load and hit limits of a program may be modified by an operator prior to beginning a swage event.

In one embodiment, the displacement limit includes an upper limit for total displacement of a needle during a swage event. In one embodiment, the load limit includes an upper limit for the total load applied to the needle during a swage event.

In one embodiment, the microprocessor is adapted to determine the total displacement of a needle during a swage event and whether the displacement limit has been exceeded. In one embodiment, the microprocessor is adapted to determine the total force subjected upon a needle during a swage event and whether the load limit has been exceeded.

In one embodiment, the microprocessor generates a message or signal that the armed surgical needle that is formed during a swage event is good if the displacement limit has been reached and the load limit has not been exceeded. In one embodiment, the microprocessor generates a message or signal that the armed surgical needle is bad if the displacement limit has not been reached and the load limit has been exceeded.

In one embodiment, each swage program may include a hit limit that corresponds to how many times the needle is hit by a swaging tool during a swage event.

In one embodiment, the servomotor and the load cell provide real time feedback to the microprocessor during a swage event. The real time feedback may be used to modify the displacement and load generated by a swaging press to increase the number of armed surgical needles that are determined to be satisfactory (i.e., satisfy all specification requirements).

In one embodiment, a program may have a second displacement limit and a second load limit for use during a second swage event, whereby the second displacement limit used during the second swage event is different than the first displacement limit used during the first swage event, and whereby the second load limit used during the second swage event is different than the first load limit used during the first swage event.

In one embodiment, the control system generates visible or audible signals to indicate whether the armed surgical needle is good or bad. In one embodiment, the control system preferably generates visible green light and an audible beep if the tested armed surgical needle is good and visible red light and an audible buzzer if the armed surgical needle is bad.

In one embodiment, a programmable swaging press for making armed surgical needles desirably includes a frame, and top and bottom swaging dies coupled with the frame, whereby the top swaging die opposes the bottom swaging die and is moveable up and down along a swaging axis that is in alignment with the bottom swaging die. In one embodiment, the programmable swaging press desirably has a load cell on the bottom swaging die for recording the load to which the bottom swaging die is subjected during a swage event, and a servomotor coupled with the top swaging die for controlling and recording the location of the top swaging die along the swaging axis. In one embodiment, the programmable swaging press preferably includes a control system with a microprocessor in communication with the load cell and the servomotor, whereby the microprocessor uses the recorded load to determine total load applied during a swage event and uses the recorded location to calculate total displacement during the swage event.

In one embodiment, the programmable swaging press desirably has a hinged mechanism including a bottom plate coupled with the frame, and a top plate overlying the bottom plate, whereby the top and bottom plates are pivotally connected to one another for enabling the top plate to pivot relative to the bottom plate, and whereby the load cell is disposed between the top and bottom plates for recording load. In one embodiment, a swaging tool is mounted on the top plate and extends toward the top swaging die along the swaging axis.

In one embodiment, a programmable swaging press preferably includes a control system with the microprocessor and having one or more swage programs stored therein for forming armed surgical needles. In one embodiment, each swage program includes a displacement limit and a load limit for use during a swage event. In one embodiment, the displacement limit has an upper limit for total displacement of a needle during a swage event, and the load limit has an upper limit for the total load to which the needle may be subjected during the swage event.

In one embodiment, the microprocessor is in communication with the servomotor for determining the total displacement of the needle during a swage event, and the microprocessor is in communication with the load cell for determining the total load to which the needle is subjected during the swage event.

In one embodiment, the microprocessor generates a message that the armed surgical needle is good if the displacement limit has been reached and the load limit has not been exceeded, and the microprocessor generates a message that the armed surgical needle is bad if the load limit has been exceeded.

In one embodiment, each swage program may include a hit limit during a swage event, whereby the hit limit is a total number of times the needle is hit during the swage event.

In one embodiment, each program stored in the control system or microprocessor may include a second displacement limit and a second load limit for use during a second swage event, whereby the second displacement limit is different than the first displacement limit, and the second load limit is different than the first load limit.

In one embodiment, a programmable swaging press for attaching surgical needles to sutures desirably has a frame, a bottom swaging die mounted on the frame, and a top swaging die mounted on the frame and being moveable up and down along a swaging axis that is in alignment with the bottom swaging die. In one embodiment, the bottom swaging die preferably has a hinged mechanism including a bottom plate coupled with the frame, a top plate overlying the bottom plate, whereby the top and bottom plates are pivotally connected to one another for enabling the top plate to pivot relative to the bottom plate, a swaging tool mounted on the top plate that extends toward the top swaging die along the swaging axis, and a load cell disposed between the top and bottom plates for recording the load to which the bottom swaging die is subjected. In one embodiment, the programmable swaging press preferably includes a control system with a servomotor coupled with the top swaging die for recording location data related to the location of the top swaging die along the swaging axis, and a microprocessor in communication with the load cell for receiving the recorded load and detecting changes in the recorded load and in communication with the servomotor for determining the location of the top swaging die along the swaging axis.

In one embodiment, a combined needle swaging and testing system preferably includes a swaging press having a die that may be used for both swaging a needle (i.e., attaching a needle to the end of a suture), and conducting a pull test on the armed surgical needle to assess the needle and suture attachment.

In one embodiment, the combined needle swaging and testing system desirably includes a control system that generates both visual and audible cues to an operator of the swage press during the testing to ensure that the needle and suture attachment is not severely overstressed or held at a high force for an extended period of time that could cause undetected damage to the needle and suture attachment.

In one embodiment, a swaging press preferably includes a system controller with a central processing unit for automatically controlling operation of the top and bottom dies of the swaging press. In one embodiment, the central processing unit desirably contains different programs for manufacturing armed surgical needles having differently sized surgical needles and differently sized sutures. In one embodiment, an operator may interact with the central processing unit for changing the parameters and limits of the programs.

In one embodiment, a swage press preferably includes upper and lower presses having respective top and bottom dies that are used for a swaging process. In one embodiment, the top die translates up and down along a swaging axis and the bottom die remains stationary. In one embodiment, both the top and bottom dies are capable of translating up and down along a swaging axis. In one embodiment, the bottom die preferably includes a hinge mechanism disposed within the lower press that is placed horizontally in the lower press and that is orthogonal to the direction of swaging. The hinge mechanism preferably has a bottom plate that is secured on the bottom die, which, in turn, is mounted on the frame of the swaging system. The hinge mechanism preferably includes a top plate that is designed and configured to receive the swage tooling. The bottom and top plates are preferably connected on one side with a precision ground rod to form a hinge and the other side of the bottom plate desirably contains a recess that is configured to accommodate a load cell. In one embodiment, during a swaging event, the hinge mechanism holds the bottom plate in place, however, after the swaging event, it serves to measure the pull force applied to a needle and suture attachment, as described herein.

In one embodiment, a motor driven programmable swaging press preferably includes a stepper or servomotor. As used herein, the term servomotor means an actuator, such as a rotary or linear actuator that enables precise control of angular or linear position, velocity and acceleration. In one embodiment, a servomotor may include a motor coupled to a sensor for providing feedback data, such as position and load feedback data. In one embodiment, the servomotor may be in communication with a central controller and/or microprocessors that are designed to receive information from the servomotors and use the information to operate the swaging press. In one embodiment, the servomotor may be controlled directly by the microprocessor to move to a pre-programmed position at a pre-programmed rate, and the servomotor may not report its position back to the microprocessor.

In one embodiment, a motor driven swaging press may include a microprocessor to analyze data signals in real time (e.g., pressure, displacement, and motor signals), a load or force measuring device (e.g., a load cell), and a system control feedback signal to control the swaging press and/or provide information (e.g., alarm notifications) to an operator.

In one embodiment, the servomotor or stepper motor is preferably connected to a top swaging die through use of a precision milled ball screw or roller screw. In one embodiment, acme screws, racks, belts or other methods may be utilized for making a connection between the servomotor and swaging dies.

In one embodiment, the top swaging die is preferably mounted on a platform, which, in turn, is mounted on a precision slide that allows for precise one-dimensional motion along a swaging axis.

In one embodiment, the bottom or lower swaging die preferably includes a hinged assembly that contains a load cell that is able to monitor the loads applied to a needle through the swaging press.

In one embodiment, a swaging press may include a force or load gauge used to determine the bottoming of the dies from which to calculate the correct standoff or "taring" of the dies.

In one embodiment, the top and bottom swaging dies may be electrically insulated and/or use capacitive touch methods to determine the bottoming of the dies.

In one embodiment, electrical conduction though the top and bottom swaging dies may be used to generate data and/or signals indicating that the top and bottom swaging dies have reached their bottom positions (e.g., home positions).

In one embodiment, the displacement data generated during a swage event may be recorded on a hard drive, a thumb drive, and/or through a network. In one embodiment, the data may be sent from a microprocessor via a Wi-Fi transmitter.

In one embodiment, the swage tooling that is connected to the top plate of the hinged mechanism desirably has an additional "testing" notch that is larger than the suture diameter, but smaller than the needle diameter. As such, after swaging a needle to a suture, the suture and attached needle may be moved a very small distance away from the location of the swage notch (e.g., 1 mm or less) to nest in the testing notch, and then the suture is pulled until the proximal end of the needle catches in the relatively smaller width testing notch. Since the top and bottom plates are connected through a hinge, as the suture is pulled, the weight of the top plate of the hinged mechanism that is translated through the load cell is lessened. This decreasing force (i.e., removal of weight from the load cell) is monitored at a rate of several thousand times per second through a microprocessor that receives load signals from the load cell.

In one embodiment, the output pins of a microprocessor are connected to a light emitting element, such as a red-green-blue (RGB) light emitting diode that can be viewed directly through a stereoscope used by the swaging operator, thus preventing the need for the operator to move his or her head and look away from the work at hand, which minimizes operator fatigue and optimizes output. In one embodiment, other microprocessor output pins may be connected to a buzzer or chime to provide audible signals to the operator. In one embodiment, an operator will receive both visual and auditory signals during swaging events that help the operator to determine whether the armed surgical needle that has been formed is acceptable or unacceptable.

In one embodiment, the programmable swaging press disclosed herein blends the capabilities of humans with the capabilities of high speed processors to greatly improve the control, efficiency, and reliability of forming armed surgical needles.

In one embodiment, the top plate overlies the load cell. In one embodiment, the load cell overlies the top plate.

In one embodiment, the swaging press may have a foot pedal to interrupt power to the load cell when the pedal is pressed and restore power after a pre-defined period of time following swaging (e.g., 500 ms).

In one embodiment, the swaging press may include audible and/or visual indicators. In one embodiment, the indicator(s) are activated when a change in load (as measured by the load cell) exceeds the force limit and/or if the total recorded displacement exceeds the displacement limit.

In one embodiment, the visual and audible indicator(s) exhibit different indications (e.g., colors, sounds, vibrations, etc.) based on whether the armed surgical needle is acceptable or unacceptable.

In one embodiment, the system may include a feedback mechanism designed to increase the force or load applied during the next swaging if a needle-suture attachment fails during the previous testing.

In one embodiment, the programmable swaging press may be partly or entirely automated.

In one embodiment, a swaging tool desirably includes an upper end having a top surface with a swaging notch for swaging a needle to a suture to form an armed surgical needle, and a testing notch, adjacent the swaging notch, for conducting a pull test on the armed surgical needle. In one embodiment, the swaging and testing notches may extend along respective longitudinal axes that are orthogonal to the swaging axis. In one embodiment, the swaging and testing notches preferably extend along respective longitudinal axes that are parallel with the top surface of the top plate and perpendicular to the swaging axis.

In one embodiment, the swaging notch desirably has a first width and the testing notch has a second width that is smaller than the first width. In one embodiment, a needle components of an armed surgical needle has a diameter that is less than or equal to the first width of the swaging notch and greater than the second width of the testing notch, and the suture component of an armed surgical needle has a diameter that is less than the first width of the swaging notch and the second width of the testing notch. In one embodiment, the first width of the swaging notch is about 8 mil, the second width of the testing notch is about 4 mil, the diameter of the needle is about 7.5-7.8 mil, and the diameter of the suture is about 3.5 mil.

In one embodiment, the control system desirably includes one or more pull test programs stored therein for conducting pull tests on armed surgical needles. Each pull test program desirably has an acceptable load range having predetermined lower and upper load limits, and an acceptable time range having predetermined lower and upper time limits for the length of a load test.

In one embodiment, a pull test program commences and/or enables a pull test inspection when a load change is detected by the microprocessor. In one embodiment, the pulling of the suture is conducted by a human that grasps the suture with his or her fingers. In one embodiment, the pull test may include an automatic inspection whereby an end of a suture is connected with an apparatus designed to pull the suture at a predetermined force and for a predetermined time. In one embodiment, a pull test program indicates that the tested armed surgical needle is acceptable if the detected load change is between the predetermined lower and upper load limits and the detected time is between the predetermined lower and upper time limits. In one embodiment, the pull test program indicates that the tested armed surgical needle is unacceptable if the detected load change is above the predetermined upper load limit. In one embodiment, the pull test program indicates that the tested armed surgical needle is unacceptable if the detected load change is between the predetermined lower and upper load limits and the detected time is above the predetermined upper time limit.

In one embodiment, during a pull test inspection of an armed surgical needle, the control system preferably generates visible or audible signals that indicate whether the tested armed surgical needle is acceptable or unacceptable. In one embodiment, the control system generates visible green light and an audible beep if the tested armed surgical needle is acceptable and visible red light and an audible buzzer if the tested armed surgical needle is unacceptable.

In one embodiment, a stereoscope is mounted on the frame for viewing the swaging and inspection notches at the top surface of the swaging tool. In one embodiment, the stereoscope desirably has at least one light emitting diode for generating visible light, such as green visible light and red visible light, to provide a test status indicator.

These and other preferred embodiments of the present invention will be described in more detail below.

DETAILED DESCRIPTION OF PREFERRED EMBODIMENTS

Figure 1:
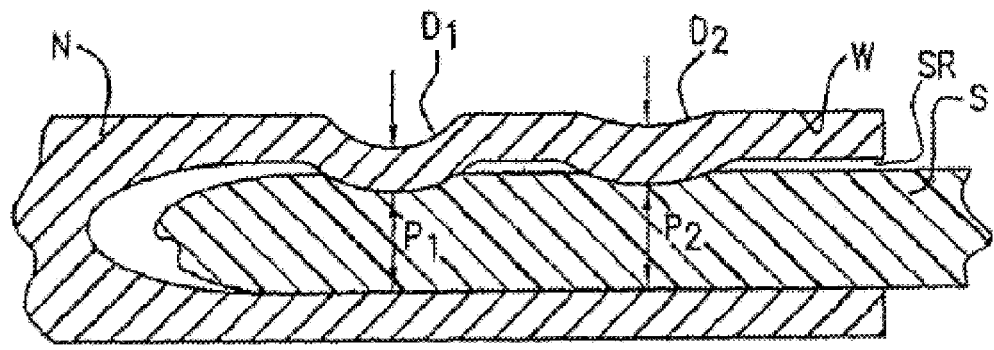
FIG. 1 shows a conventional method of swaging a needle to a suture.
Figure 2:
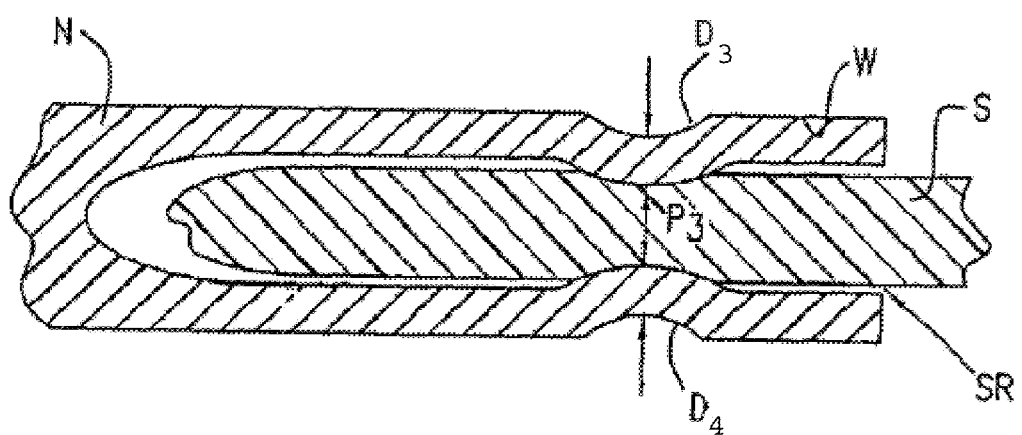
FIG. 2 shows a second conventional method of swaging a suture to a needle.
Figure 3:
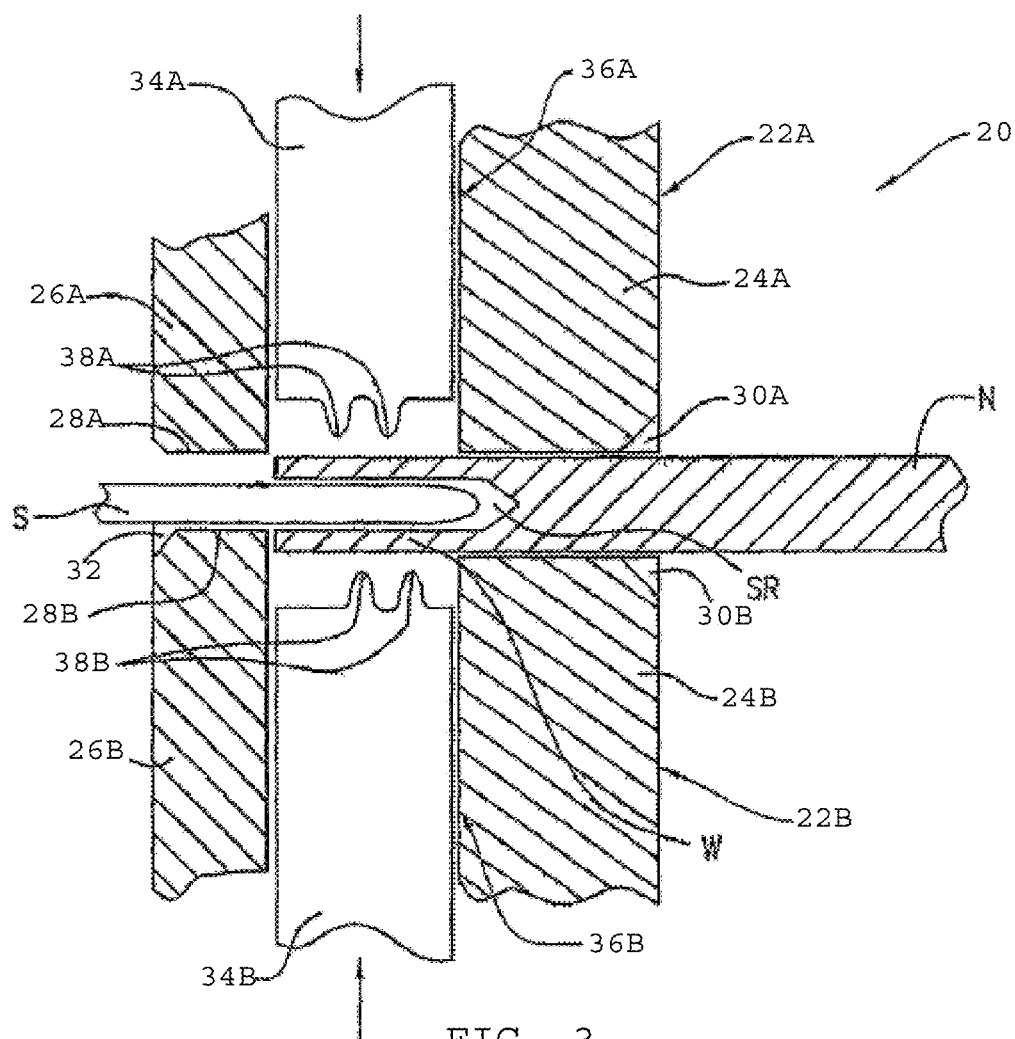
FIG. 3 shows a prior art needle swaging press assembly having first and second swage dies that converge to attached a needle to a suture.
Figure 4:
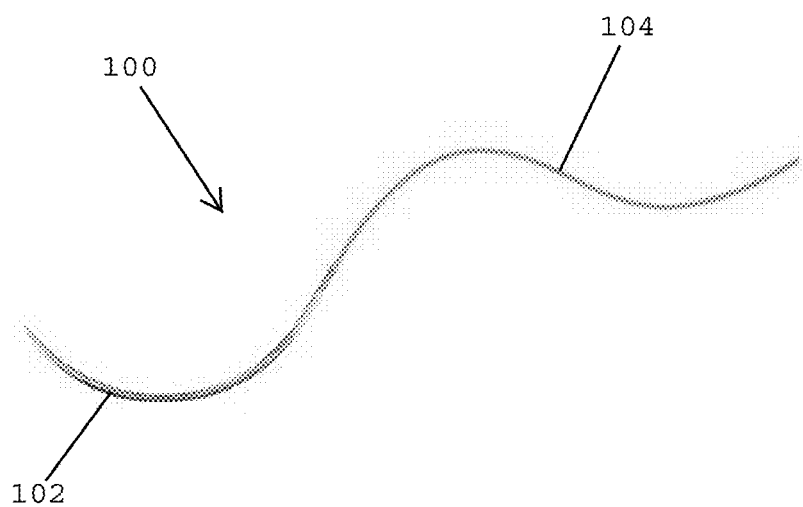
FIG. 4 shows an armed surgical needle including a needle and a suture, in accordance with one embodiment of the present patent application.

Referring to FIG. 4, in one embodiment, an armed surgical needle 100 preferably includes a surgical needle 102 that is secured to the end of a suture 104. In one embodiment, the needle 102 is made of a broad variety of rugged materials including metal alloys such as stainless steel, 4310 SS, nickel-titanium (NiTi) SS and 420 SS, or advanced alloys, such as, tungsten-rhenium (W—Re) alloys or similar refractory alloys. In one embodiment, the needle 102 is made of a tungsten-rhenium alloy that is sold under the trademark EVERPOINT® by Ethicon, Inc. of Somerville, N.J.

In one embodiment the suture material may be made of conventional, biocompatible, absorbable materials, non-absorbable materials, and combinations of absorbable and non-absorbable materials. Preferred non-absorbable materials include polypropylene, a polymer blend of polyvinylidene fluoride and polyvinylidene fluoride-co-hexafluoropropylene, polyesters, polyethylene, polyvinylidene fluoride (PVDF), polyesters, polyethylene terephthalate, glycol-modified polyethylene terephthalate, polytetrafluoroethylene, fluoropolymers, nylons etc. and the like, or copolymers of combinations thereof. Preferred absorbable polymeric materials include polydioxanone, polyglactin, polyglycolic acid, copolymers of glycolide and lactide, polyoxaesters, and poliglecaprone. In certain preferred embodiments, the suture material may include combinations of both absorbable and non-absorbable materials. In addition, metals may be suitable for certain applications, such as instances where specific strength, electric conductivity or corrosion resistance is necessary. In one preferred embodiment, the suture material preferably includes a polymer blend of polyvinylidene fluoride and polyvinylidene fluoride-co-hexafluoropropylene material. In addition, any of these materials may have conventional surface modifications that include coatings, plasma treatments, therapeutics, and the like. In one embodiment, the needle 102 is coated with a silicon coating. In one embodiment, the suture 104 is a polypropylene suture sold under the trademark PROLENE® by Ethicon, Inc of Somerville, N.J.

Figure 5A:
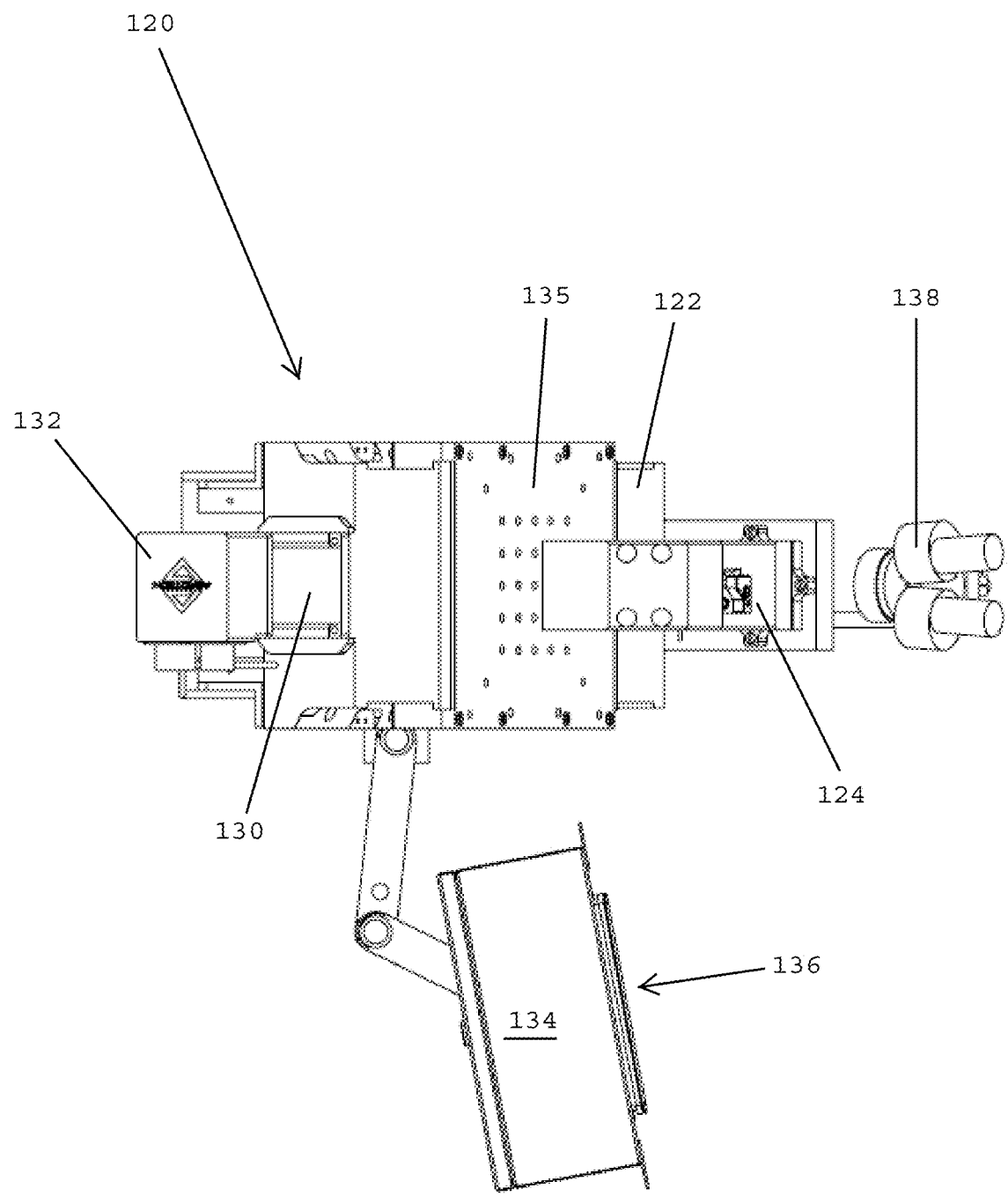
FIGS. 5A-5C show a programmable swaging press for attaching surgical needles to sutures including a top swaging die and a bottom swaging die, in accordance with one embodiment of the present patent application.
Figure 5B:
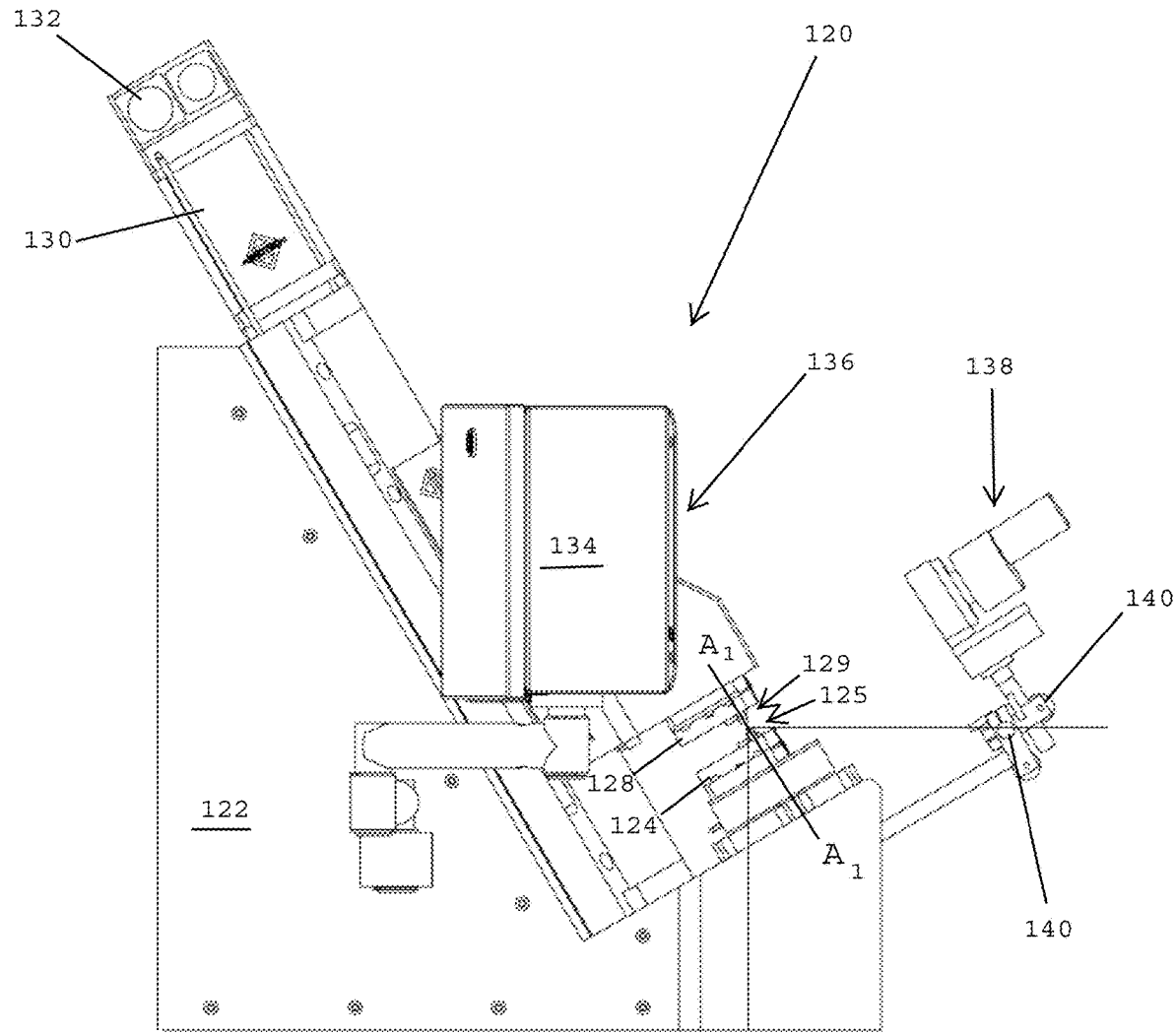
Figure 5C:
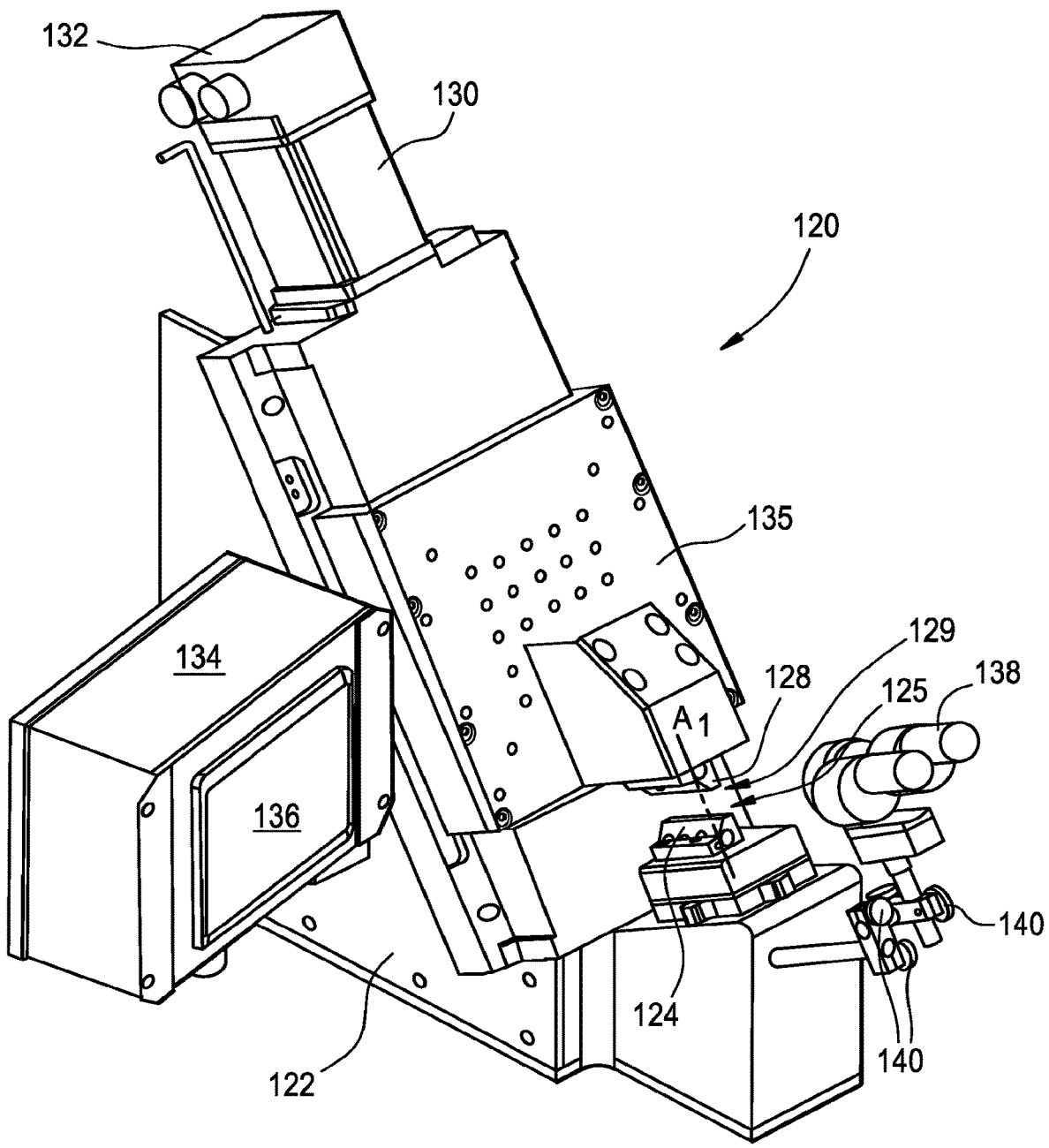

Referring to FIGS. 5A-5C, in one embodiment, a swaging press 120 for making armed surgical needles preferably includes a frame 122 having a bottom die holder block 124 with a bottom swaging die 125 mounted thereon, and a top die block holder 128 having a top swaging die 129 that is adapted to move up and down along a swaging axis $A_1$ that is aligned with the bottom swaging die 125. In one embodiment, the top swaging die 129 is mounted on a precision slide 135 that is configured to slide up and down on the frame 122. The swaging press 120 desirably includes a servomotor 130 that is activated for moving the precision slide 135, the top die block holder 128, and the top swaging die 129 up and down along the swaging axis $A_1$ relative to the bottom swaging die 125. The swaging press system 120 preferably includes a power connection 132 for the servomotor 130. The power connection 132 may house an encoder that provides position feedback information for the top swaging die 129.

In one embodiment, the programmable swaging press 120 preferably includes a human machine interface (HMI) 134 that is connected to and/or positioned adjacent the frame 122. In one embodiment, the HMI 134 desirably has an LCD display 136 (e.g., a touch-screen monitor) that enables an operator to interface with the HMI 134 for selecting a particular swaging program and/or monitoring a swaging operation. In one embodiment, the HMI 134 preferably houses a control system having one or more microprocessors, memory devices, and programs for operating the swaging system 120. In one embodiment, the HMI 134 desirably has numerous programs and/or subroutines loaded therein that may be selected by an operator so that the swaging system 120 may be utilized for making a wide range of armed surgical needles having needles with a range of different sizes and suture material having a range of different sizes.

In one embodiment, the programmable swaging press 120 desirably includes a stereoscope 138 that is mounted to the frame 122. The stereoscope 138 is preferably aimed at the bottom die 125 for using during swaging operations, as will be described in more detail herein. The stereoscope 138 desirably includes optics that provide for a magnified view of the needles, suture material, and opposing dies during swaging operations. In one embodiment, the stereoscope 138 may include adjustment knobs 140 for tightening the stereoscope holder for holding the position of the stereoscope.

In one embodiment, the stereoscope 138 may include one or more light generating elements, such as red-green-blue (RGB) light emitting diodes, that may be viewed directly through the stereoscope used by the swaging operator for the purpose of attachment inspection, thus eliminating the need for the operator to move his or her head and look away from the work at hand. In one embodiment, the light emitting diode (e.g., an RGB diode) may be mounted on the bottom die holder block 124 (FIG. 5C). The benefit of providing light emitting diodes on the stereoscope or the bottom die holder block is related to minimizing operator fatigue and optimizing output. In one embodiment, microprocessor output pins are connected to an audible signal generator, such as a beeper or buzzer, to provide audible signals or sounds for an operator of the swaging system. As such, an operator may receive both visual and auditory signals during a swaging operation or event that help the operator to insure that the proper prescribed displacement and load is being applied.

In one embodiment, the red-green-blue light emitting diodes within the stereoscope 138 are in communication with the control system 200 (FIG. 9) within the HMI 134 (FIG. 5C).

Figure 6A:
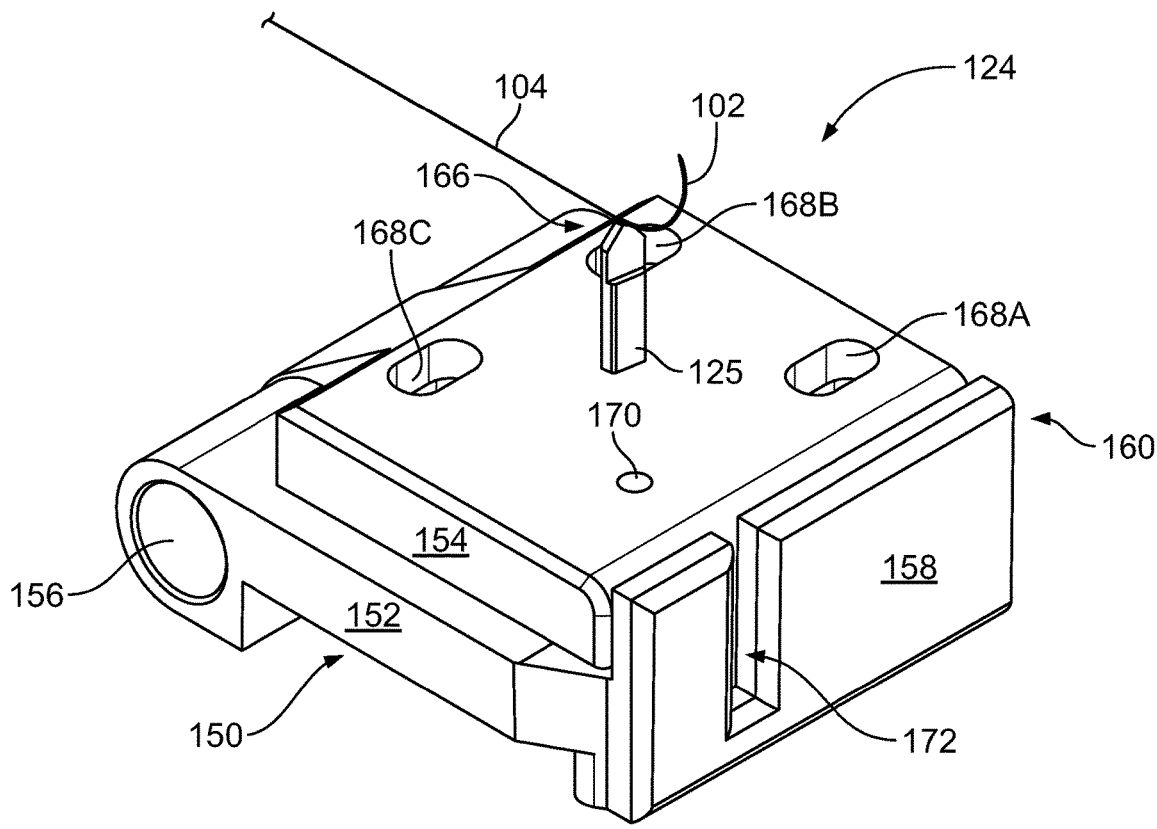
FIG. 6A shows a perspective view of a hinged assembly of the bottom swaging die shown in FIGS. 5A-5C, in accordance with one embodiment of the present patent application.
Figure 6B:
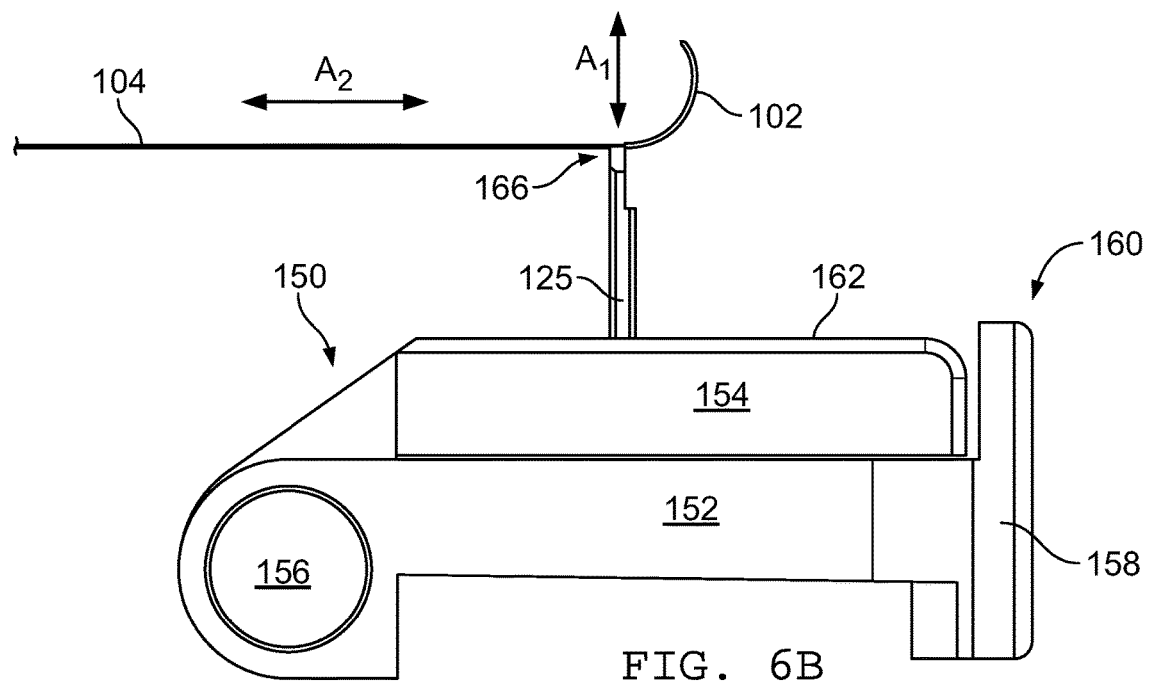
FIG. 6B shows a side elevation view of the hinged assembly of the bottom swaging die shown in FIG. 6A.

Referring to FIGS. 6A and 6B, in one embodiment, the swaging system preferably includes a hinged mechanism 150 that is coupled with the bottom swaging die 125 (FIGS. 5B and 5C). In one embodiment, the hinged mechanism 150 is desirably placed horizontally in the bottom die and orthogonal to the direction of the swaging axis $A_1$ (FIGS. 5B, 5C and 6B). In one embodiment, the hinged mechanism 150 desirably includes a bottom plate 152 that is mounted to the bottom die and a top plate 154 that overlies the bottom plate 152. The hinged mechanism 150 preferably includes a hinge 156 that enables the top plate 154 to pivot about the hinge 156 relative to the bottom plate 152. In one embodiment, the hinged mechanism 150 may include bearings or bushings in contact with the hinge 156 for minimizing friction as the top plate 154 pivots and moves relative to the bottom plate 152.

In one embodiment, the hinged mechanism 150 preferably includes a guard 158 that is secured to or made integral with an end of the bottom plate 152 on a side of the bottom plate that is opposite the hinge 156. In one embodiment, the guard 158 has an upper end 160 that projects above a top surface 162 of the top plate 154 to prevent an operator from inadvertently bumping into and/or contacting the top half 154 thereby sending an erroneous signal from the load cell 174 to the microprocessor.

In one embodiment, the hinged mechanism 150 preferably includes a swaging tool 164 projecting upwardly from the top surface 162 of the top plate 154. In one embodiment, the swaging tool 164 desirably has an upper end 166 that is adapted to receive a needle 102 and a suture 104 for attaching the needle to the suture. In one embodiment, the upper end 166 of the swaging tool 164 has a first notch for swaging the needle 102 to the suture 104 (i.e., the swaging notch), and a second notch, adjacent the first notch, for inspecting the attachment of the needle 102 to the suture 104 (i.e., the inspection notch).

Referring to FIG. 6A, in one embodiment, the top plate 154 of the hinged mechanism 124 desirably includes openings 168A-1680 that are utilized for securing a swaging tool support plate over the top surface 162 of the top plate 154 for providing support for the base of the swaging tool 164 projecting from the top surface of the top plate. In one embodiment, the top plate 154 also preferably includes a set-screw opening 170 formed in the top surface 162 of the top plate that provides access to a set screw on a load cell disposed within the bottom plate 152, as will be described in more detail herein.

In one embodiment, the guard 158 desirably has an opening 172 formed therein that enables conductive elements, conductive conduits, and/or conductive leads to pass therethrough for interconnecting the load cell of the hinged mechanism with a microprocessor and/or system controller.

Figure 7:
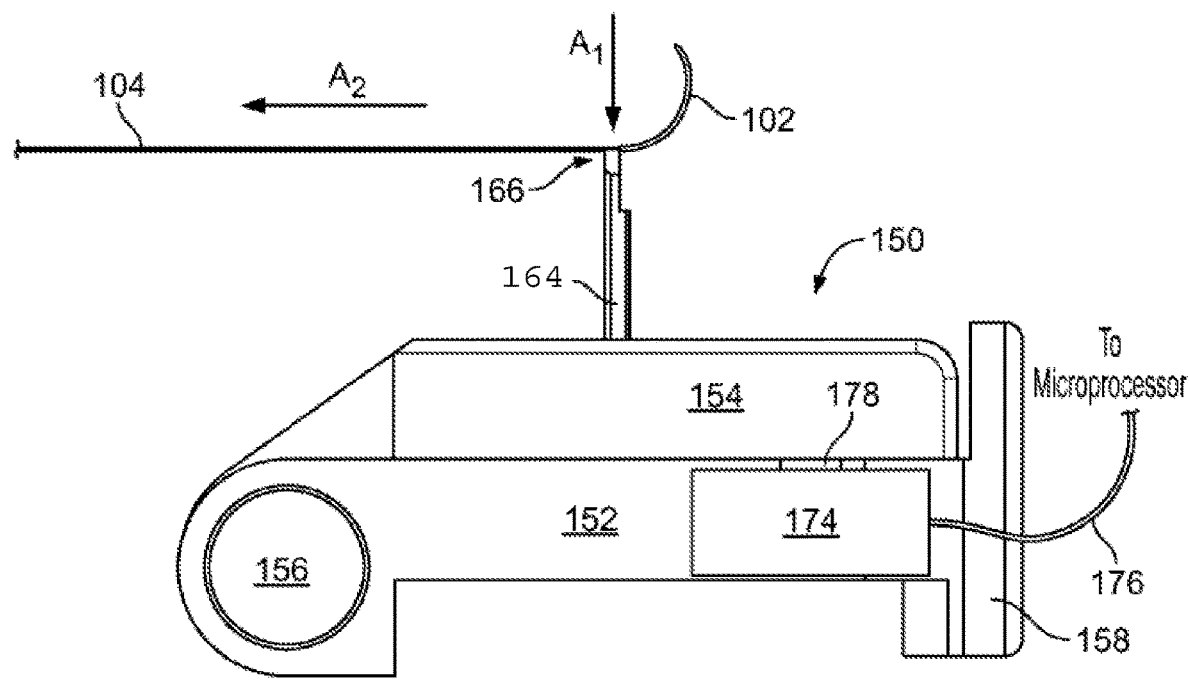
FIG. 7 shows a partial cross sectional view of the hinged assembly shown in FIGS. 6A and 6B including a swage tool, and a load cell disposed between top and bottom plates of the hinged assembly, in accordance with one embodiment of the present patent application.

Referring to FIG. 7, in one embodiment, the hinged mechanism 150 preferably includes a load cell 174 disposed in the bottom plate 152 of the hinged mechanism, which, in turn, is mounted to the bottom die holder block 124 (FIG. 5C). The load cell 174 is preferably coupled with a conductive lead 176 that passes through the opening 172 (FIG. 6A) of the guard 158. The conductive lead 176 is desirably interconnected with a microprocessor and/or a system controller for communicating with the load cell 174. In one embodiment, the load cell 174 preferably has an adjustable set screw 178 that is in alignment with the set screw opening 170 (FIG. 6A) accessible at the top surface 162 of the top plate 154.

In one embodiment, the load cell 174 is a transducer that is used to create an electrical signal whose magnitude is directly proportional to the force or load being measured. The load cell may be a piezoelectric load cell, a strain gauge load cell and combinations thereof.

During a swaging process, the hinged mechanism 150 holds the swaging tool 164 in place. The load cell 174 records the load applied to a needle during a swage event.

In one embodiment, directly after swaging, the hinged mechanism is configured to measure the pull force exerted upon an armed surgical needle. In one embodiment, in addition to a swaging notch, the upper end 166 of the swaging tool 164 also has a testing notch adjacent the swaging notch that is larger than the diameter of the suture 104 but smaller than the diameter of the needle 102. In this way, after swaging, the suture 104 may be moved a very small distance away from the swaging notch location (e.g. 1 millimeter or less) to the testing notch location.

For testing the armed surgical needle, the suture 104 is pulled in the direction designated $A_2$ in FIG. 7 until the proximal end of the needle 102 catches the testing notch. Axis $A_1$ shows the swaging direction of motion and the direction of gravity. Axis $A_2$ shows the direction that the suture 104 is pulled when the suture (attached to the needle 102) is positioned within the testing notch and the proximal end of the needle 102 engages an end of the relatively smaller diameter testing notch. Since the top plate 154 is connected to the hinged mechanism 150 via the hinge 156, as the suture 104 is pulled in the direction designated $A_2$, the weight of the top plate 154 that is translated through the load cell 174 is lessened. This decreasing load (i.e. removal of weight from the load cell 174) is monitored at a rate of several thousand times per second through a microprocessor in the control system that receives the signals from the load cell.

Figure 8:
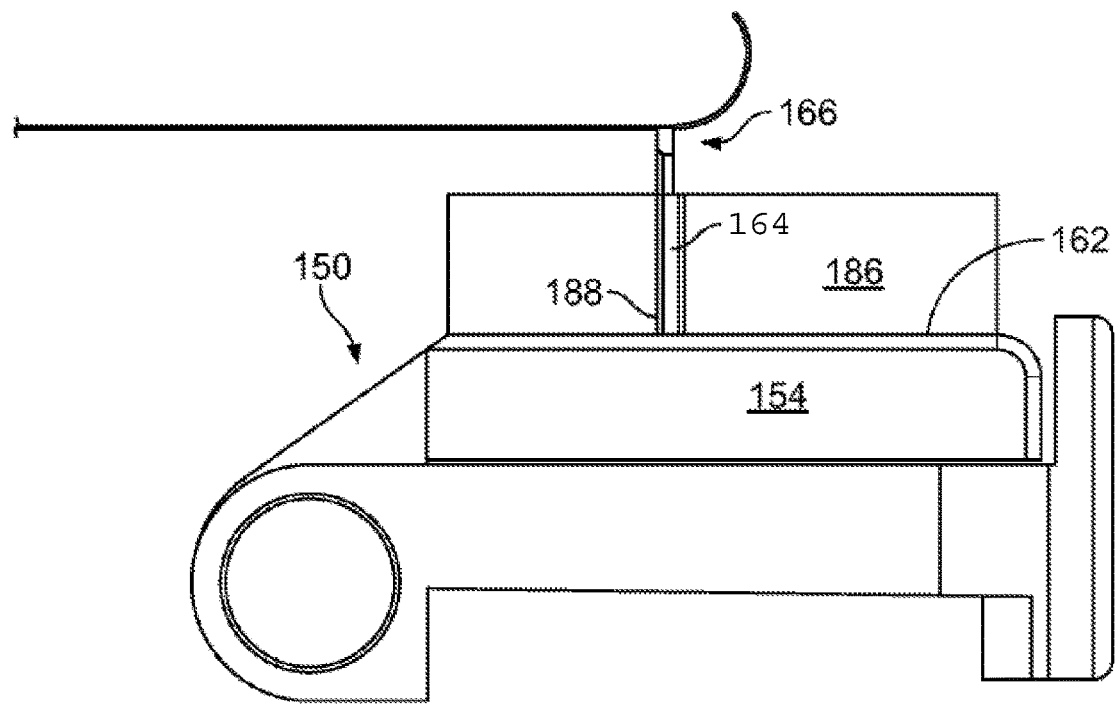
FIG. 8 shows a hinged assembly of a bottom swaging die, in accordance with one embodiment of the present patent application.

Referring to FIG. 8, in one embodiment, the hinged mechanism 150 desirably includes a swaging tool support plate or die holder 186 that is positioned over the top surface 162 of the top plate 154. In one embodiment, the swaging tool support plate may include projections that are inserted into the swaging tool support plate openings 168A-168C (FIG. 6A). In one embodiment, the swaging tool support plate 186 includes an opening 188 that enables the swaging tool 164 to pass therethrough with the upper end 166 of the swaging tool 164 projecting above the swaging tool support plate 186 to be accessible for swaging and testing operations. The swaging tool support plate 186 preferably supports and maintains the integrity of the swaging tool 164 during swaging operations.

Figure 9:
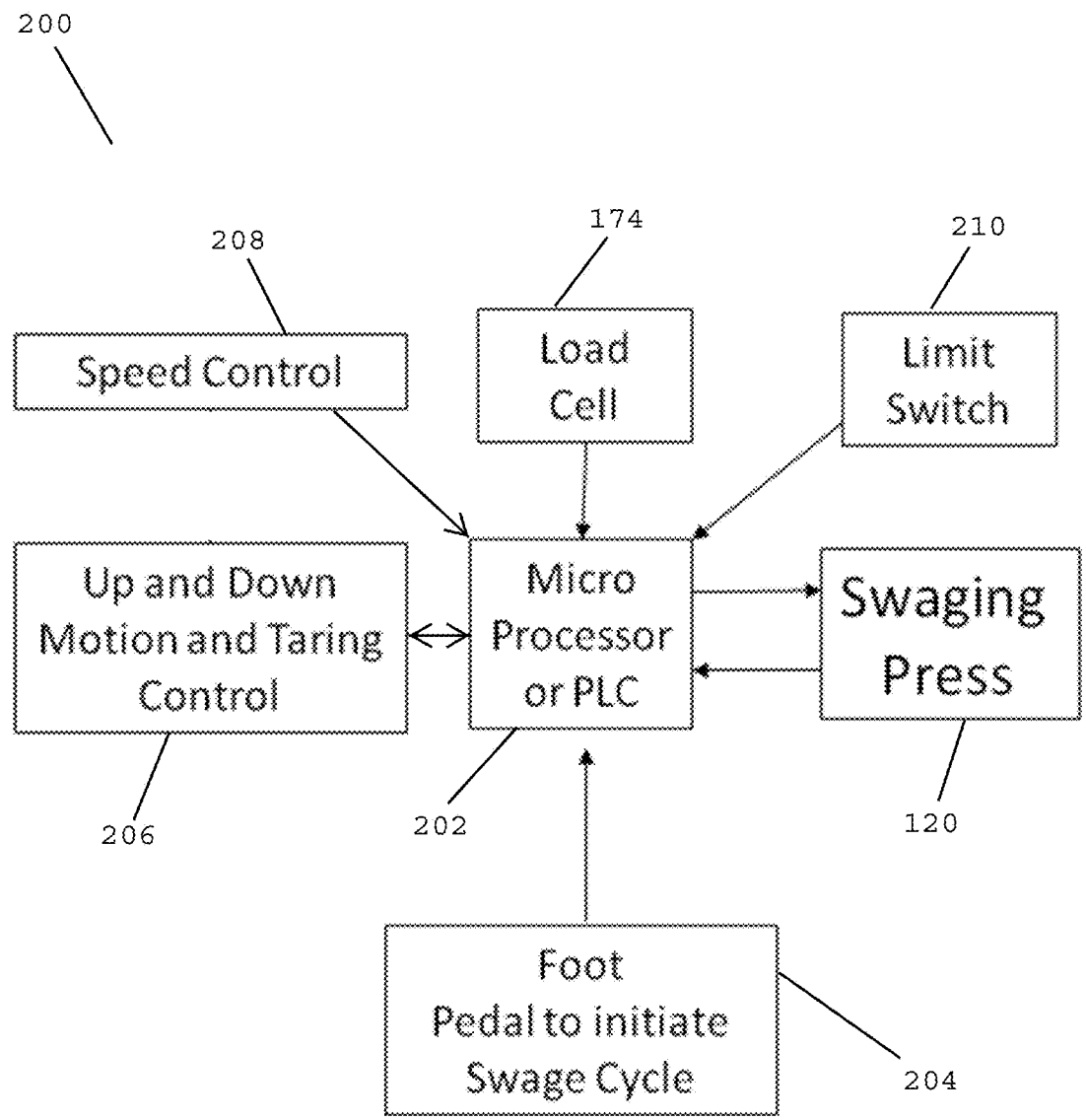
FIG. 9 is a schematic diagram of a control system for a programmable motor driven swaging press, in accordance with one embodiment of the present patent application.

Referring to FIGS. 5C and 9, in one embodiment, the HMI 134 preferably contains one or more swaging programs stored therein. In one embodiment, the swaging press may be utilized to swage needles and sutures having different dimensions, sizes, properties and/or configurations. In one embodiment, an operator may select a swaging program from a menu of different programs pre-loaded into a microprocessor. In one embodiment, an operator has the ability to modify the parameters of a program such as changing the total displacement limit, the total load limit, and/or the number of hits on a needle during a single swage event. In one embodiment, an operator preferably interacts with an LCD touchscreen on the HMI for selecting a particular program for utilization. The program that is utilized may change depending upon the sizes of the needles and sutures being used to form armed surgical needles, or the particular surgical function that will be performed using an armed surgical needle.

Referring to FIG. 9, in one embodiment, a control system 200 for a programmable motor driven swaging press preferably includes a microprocessor or programmable logic controller 202 that is in communication with a foot pedal 204 utilized to initiate a single swage event. As used herein, the terminology "single swage event" means activating a swage press to move a die from an open position to a closed position to compress the outer wall of a needle and apply a load to the outer wall of a needle and then return to an open position. In one embodiment, a single swage event may include swaging tools hitting and/or tapping on the outer wall of the needle multiple times as the swaging tools remain close to the outer wall and before the dies return to an original open position.

In one embodiment, the microprocessor 202 is desirably in two-way communication with a swaging press (FIGS. 5A-5C) that opens and closes the top and bottom dies in response to activation of the foot pedal 204. The control system preferably includes a servomotor 206 coupled with a precision slide that continuously monitors the exact location of the top and bottom dies relative to one another along a swaging axis. The servomotor communicates with the microprocessor to continuously report the location data for the dies to the microprocessor. The servomotor and the microprocessor interact to provide up and down motion and taring control of the top and bottom dies. In one embodiment, the taring control function is utilized to find a zero point and/or home position for the top and bottom dies of the swaging press. In one embodiment, the dies initially move to a fully closed position to be placed in the home position, whereby the microprocessor is able to calibrate the system and confirm the exact location of the top and bottom dies relative to one another. In one embodiment, the dies may move to a fully open position for initial calibration and/or to confirm the exact location of the top and bottom dies relative to one another.

In one embodiment, the system controller 200 desirably includes a speed control 208 that may be adjusted by an operator and/or the microprocessor 202 for controlling the speed and acceleration at which the swaging press dies open and close.

In one embodiment, the bottom die of the swaging press preferably includes a load cell 174 (FIG. 7) that records the load applied to the bottom die when the top and bottom dies are in a closed configuration for swaging a needle to a suture.

In one embodiment, the system controller 200 desirably includes a limit switch 210 that may be engaged by an operator for adjusting the program to define the maximum first swage event displacement, the maximum first swage event force safety limit, and the number of cycles should a multi-hit, jackhammer process be desired within a single swage event. The limit switch desirably enables an operator to select, control and/or adjust the limits for the total displacement of the outer wall of the needle, the total force or load applied to the outer wall of the needle and the number of times the swaging tool hits the outer wall of the needle. In one embodiment, the control system also enables an operator to use a first set of limits for a first swage event, and a second set of limits for a second swage event. In one embodiment, swaging a needle to a suture may comprise a plurality of swaging events on a single needle whereby the displacement, force and hit limits are different for two or more of the swage events. In one embodiment, the needle may be slightly rotated between each swage event so that the swaging tools contact a different area on the outer surface of the wall of the needle.

Figure 10:
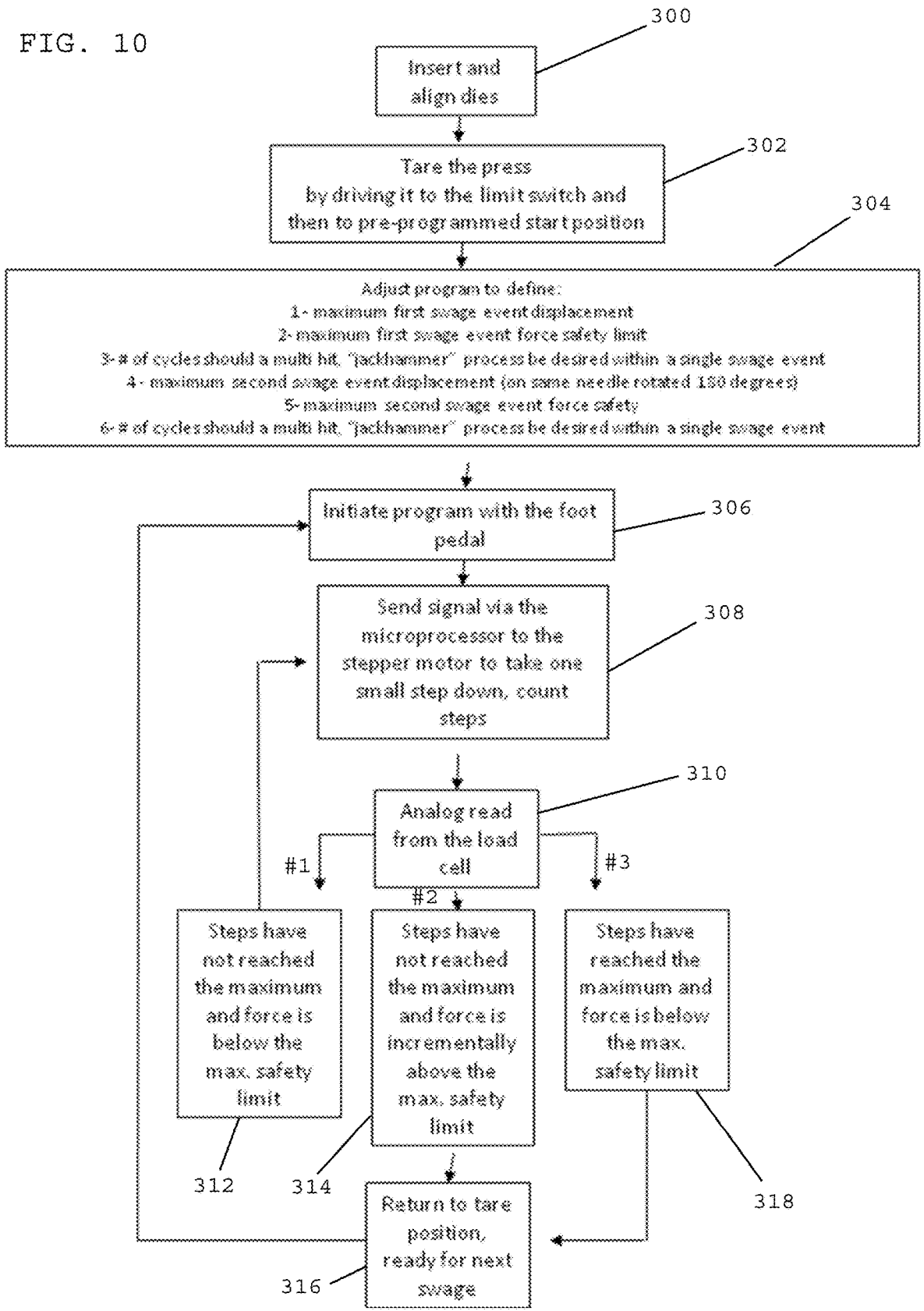
FIG. 10 illustrates a flowchart for a program used for operating a swaging press and recording total displacement and total load, in accordance with one embodiment of the present patent application.

FIG. 10 illustrates a program for operating a programmable swaging press, in accordance with one embodiment of the present invention. The program may be loaded into a system controller and/or one or more microprocessors. In one embodiment, a swaging press may be pre-loaded with a plurality of different programs for swaging needles and sutures having different sizes and functions.

In one embodiment, the program desirably includes a first stage 300 in which the top and bottom dies are inserted into the swaging press and aligned with one another along a swaging axis. In one embodiment, the operator initiates a taring event by either engaging an actuator (e.g., pressing a button switch) or by engaging the HMI 134 (FIG. 5C), thereby causing the servomotor to drive the press until the limit switch is encountered and tripped, thus establishing an exact known position defining the displacement of the swaging dies from one another.

In one embodiment, at a stage designated 302, the swaging press is tared by moving the top and bottom dies to a fully closed position, and then to a pre-programmed start position. In one embodiment, after the swaging press is turned on, the dies are moved to the fully open position so as to orient the system controller and confirm the home position for the top and bottom dies. Once the home position has been located and confirmed by the system controller, the top and bottom dies generally move back toward one another to an initial pre-programmed start position for commencing a swage event.

In one embodiment, at stage 304, an operator may adjust the program limits and/or select a pre-programmed operational protocol for operating the swaging press. The control system is preferably adjusted and/or pre-programmed to define a number of variables including a maximum first swage event displacement, a maximum first swage event force safety limit, and the number of times the swaging tool(s) should hit the outer wall of the needle within a single swage event. In other words, after the foot pedal is depressed, a multi-hit process may result in the needle being tapped multiple times after the dies close. In one embodiment, a program may be selected whereby a swaging tool hits the outer wall of a needle three times during a first swage event, and four times during a second swage event.

In one embodiment, at stage 304, each time a swaging event takes place (e.g., activated by depressing the pedal), an operator may control and/or modify the displacement limit, the force limit, and the number of hits. In one embodiment, the amount of displacement may be more during a second swage event than a first swage event. In one embodiment, the force limit may change from the first swage event to the second swage event. In one embodiment, three or more swage events may occur during the stage designated 304. The needle may be rotated between each swage event.

In one embodiment, at stage 306, an operator initiates a swage event by depressing a foot pedal. After the foot pedal has been depressed, at stage 308, the microprocessor sends a signal to the servomotor to begin to move the top and bottom dies toward a closed position for displacing the walls of a needle, applying a force and/or load on the walls of the needle, and tapping the walls of the needle one or more times. In one embodiment, the servomotor is in continuous communication with the microprocessor for reporting the locations of the top and bottom dies. The location information may be used to calculate the total displacement of the needle located between the dies. In one embodiment, the servo motor may send 1,000 readings to the microprocessor in less than one second.

In one embodiment, at stage 310, the load cell on the bottom die preferably obtains load readings that indicate the amount of force applied to the walls of the needle. In one embodiment, the load cell may obtain thousands or tens of thousands of load readings is less than one second and transmit the load reading information to the microprocessor for monitoring and calculating total load applied during a single swage event. The control system and the microprocessor continuously receive the displacement and load data to determine whether an armed surgical needle is good (i.e., the displacement and load limits have not been exceeded) or bad (i.e., the displacement limit or the load limit has been exceeded).

In one embodiment, the control system program desirably includes at least three different scenarios designated #1, #2, and #3. In scenario #1, at step 312, the servomotor transmits information to the microprocessor indicating that the dies have not reached the maximum displacement limit, and the load cell transmits information to the microprocessor that the force applied to the needle remains below predetermined force limit. Because the displacement limit and the force limit have not been reached, the system controller continues to close the dies and apply more force to the needle until the system determines that the displacement limit and the force limit have been reached. The control system repeats the steps until the predetermined displacement limit, the predetermined force limit, and the preferred number of hits on the needle has been obtained within the single swage event.

In scenario #2, the stage designed 314, the microprocessor obtains readings from the servomotor indicating that the displacement limit has not been reached, and the microprocessor obtains readings from the load cell that the total load applied to the needle is above the preferred load limit. In this scenario, the microprocessor will determine that too much load has been applied to the needle and will issue a command that the armed surgical needle is defective/bad. Upon detecting that the armed surgical needle is bad, the microprocessor will activate a light and/or audible sound to notify an operator that the armed surgical needle is defective and should be discarded. In one embodiment, the control system generates a red light and/or an audible buzzer at the stereoscope to inform a swaging press operator that the armed surgical needle is defective and should be discarded. At stage 316, after the microprocessor has recognized that a defective product has been formed, the system controller will return the swage press to the pre-programmed start position for the top and bottom dies to commence a subsequent swage event.

In scenario #3, at the stage designated 318, the servomotor sends signals to the microprocessor that the pre-set displacement limit has been obtained, and the load cell sends signals to the microprocessor that total force applied to the needle is below the force/load limit. Upon receiving the information, the microprocessor will determine that the armed surgical needle is good, and the microprocessor will generate visible and/or audible signals that inform the operator that the armed surgical needle produced during the swage event is good. In one embodiment, the microprocessor and/or the control system may generate a green light and a positive audible signal at the stereoscope to inform the swaging press operator that the product is good. In one embodiment, after the good signals are sent, the control system may return the swaging press dies back to their original start position to be ready for the next swaging event.

In one embodiment, a stereoscope for a swaging press may include one or more light emitting diodes that are capable of generating various colors including green, yellow and red light. In one embodiment, green light is generated when an acceptable product has been formed. In one embodiment, a red light is generated when a defective product has been formed to indicate that the product should be discarded. In one embodiment, a yellow light is generated to indicate that the displacement limit, the force limit, and/or the total number of desired hits/taps of the needle have not yet been attained.

In one embodiment, the microprocessor is capable of obtaining one thousand readings from the load cell within a period of 0.5 seconds, and 1,000 readings from the servo motor within 0.5 seconds. As a result, during a single swage event, the microprocessor is continuously monitoring the status of the displacement limit, the force limit, and the number of hits applied to a needle.

In one embodiment, a needle may be rotated (e.g., 180 degrees) between a first swage event and a second swage event. In one embodiment, a needle may be rotated 90 degrees between a first and second swage event, another 90 degrees between a second and third swage event, and yet another 90 degrees between a third and fourth swage event. The displacement limit, force limit, and number of hits limit may change between swage events, and the changes may be pre-programmed into the control system and/or microprocessors. In other embodiments, to make an armed surgical needle, a single needle may be rotated between one to twelve times or more for different swage events.

In one embodiment, the precision slide and/or the top and bottom dies may include a precision, programmable electric actuator that incorporates moving coil technology, also known as voice coil actuator technology. In one embodiment, the precision slide and/or top and bottom dies may incorporate moving coil technology that is similar to that sold by SMAC Corporation of Carlsbad, Calif. See www.s-mac-mca.com/technical-resources/moving-coil-technology.

Programmable electric actuators incorporating moving coil technology provide numerous benefits over conventional electric cylinder actuators including 1) enabling force, position, and speed to be totally programmable, 2) perform at exceptionally high speeds or very low speeds, 3) perform with sub-micron accuracy and repeatability, and 4) provide extremely accurate sensing of product location and/or dimensions.

Programmable electric actuators incorporating moving coil technology are preferred for a wide range of high cycle positioning, measuring, inspection, and pick and place applications. Manufacturers desiring to increase production time, simplify set-up, and facilitate making "on the fly" adjustments to a swaging press during production runs may dramatically improve performance by using programmable electric actuators incorporating moving coil technology.

In one embodiment, the voice coil sits in a strong magnetic field, and a current may be passed through the coil for generating a force in either direction. The amount of force that is generated by the moving coil device is governed by the equation:

$$F \propto NIB \text{ where:}$$

F is the force generated;
N is the number of turns in the winding (Constant);
I is the current flowing through the winding; and
B is the magnetic flux (Constant).

Therefore, by controlling current, the force output may be accurately controlled.

Programmable electric actuators incorporating moving coil technology provide an ability to switch between operations—force, position and velocity mode—at any time; provide "on the fly" adjustable movement for quick changeover; provide for constant force monitoring and control; and can be programmed to decelerate smoothly and quickly so that mechanical slamming is totally eliminated.

Programmable electric actuators incorporating moving coil technology are programmable in force, acceleration and velocity, thereby providing an ability to run various products with a quick changeover using a control system, a controller, or central processing unit (CPU). A broad variety of different motion profiles and programs may be stored and preset in a control system. In one embodiment, a programmable electric actuator incorporating moving coil technology may operate in different modes: 1) Force Mode. 2) Velocity Mode: Velocity Mode allows the top and bottom dies to be moved with a given velocity, acceleration, force and direction. 3) Position Mode: Position Mode will allow the top and bottom dies to be moved to various positions along the swaging axis using acceleration, velocity and force. In one embodiment, it is possible to perform absolute, relative and "learned position" moves.

While the foregoing is directed to embodiments of the present invention, other and further embodiments of the invention may be devised without departing from the basic scope thereof, which is only limited by the scope of the claims that follow. For example, the present invention contemplates that any of the features shown in any of the embodiments described herein, or incorporated by reference herein, may be incorporated with any of the features shown in any of the other embodiments described herein, or incorporated by reference herein, and still fall within the scope of the present invention.

What is claimed is:

1. A programmable swaging press for attaching surgical needles to sutures comprising:
    a bottom swaging die;
    a top swaging die opposing said bottom swaging die and being moveable up and down along a swaging axis that is aligned with said bottom swaging die;
    a load cell on said bottom swaging die for recording load data;
    a servomotor coupled with said top swaging die for recording location data that corresponds to the location of said top swaging die on the swaging axis;
    a control system comprising a microprocessor in communication with said load cell and said servomotor, wherein said microprocessor uses said recorded load data to determine a total load applied during a swage event, and wherein said microprocessor uses said recorded location data to calculate a total displacement during the swage event;
    wherein said bottom swaging die comprises a hinged mechanism including a bottom plate and a top plate overlying said bottom plate, wherein said top and bottom plates are pivotally connected to one another for enabling said top plate to pivot relative to said bottom plate, wherein said load cell is disposed between said top and bottom plates and is adapted to send said recorded load data to said microprocessor.

2. The programmable swaging press as claimed in claim 1, further comprising:
    a frame;
    a guide rail secured to said frame;
    a precision slide coupled with said guide rail for moving between upper and lower ends of said guide rail;
    said top swaging die being mounted on said precision slide;
    said servomotor being coupled with said precision slide for controlling up and down movement of said precision slide between the upper and lower ends of said guide rail, which, in turn, controls up and down movement of said top swaging die along the swaging axis.

3. The programmable swaging press as claimed in claim 1, wherein said servomotor and said load cell provide real time feedback to said microprocessor during the swage event.

4. The programmable swaging press as claimed in claim 1, wherein said top swaging die is mounted on a precision slide that is coupled with said servomotor for controlling one-dimensional, up and down movement of said top swaging die along the swaging axis.

5. The programmable swaging press as claimed in claim 1, wherein said control system comprises one or more swage programs stored therein for forming armed surgical needles, wherein each said swage program comprises a displacement limit and a load limit for use during a swage event.

6. The programmable swaging press as claimed in claim 5, wherein each said program comprises a second displacement limit and a second load limit for use during a second swage event, wherein said second displacement limit is different than said first displacement limit, and wherein said second load limit is different than said first load limit.

7. The programmable swaging press as claimed in claim 5, wherein said control system generates visible or audible signals to indicate whether said armed surgical needle is good or bad.

8. The programmable swaging press as claimed in claim 7, wherein said control system generates visible green light and an audible beep if said tested armed surgical needle is good and visible red light and an audible buzzer if said armed surgical needle is bad.

9. The programmable swaging press as claimed in claim 5, wherein said displacement limit comprises an upper limit for the total displacement of a needle during the swage event, and wherein said load limit comprises an upper limit for the total load applied to said needle during the swage event.

10. The programmable swaging press as claimed in claim 9, wherein said microprocessor determines the total displacement of said needle during the swage event and whether the displacement limit has been exceeded and the total force subjected upon said needle during the swage event and whether the load limit has been exceeded.

11. The programmable swaging press as claimed in claim 10, wherein said microprocessor generates a message that said armed surgical needle is good if the displacement limit has been reached and the load limit has not been exceeded, and wherein said microprocessor generates a message that said armed surgical needle is bad if the displacement limit has not been reached and the load limit has been exceeded.

12. The programmable swaging press as claimed in claim 11, wherein each said swage program further comprises a hit limit corresponding to how many times said needle is hit by a swaging tool during the swage event.

13. A programmable swaging press for making armed surgical needles comprising:
- a frame;
- top and bottom swaging dies coupled with said frame, wherein said top swaging die opposes said bottom swaging die and is moveable up and down along a swaging axis that is in alignment with said bottom swaging die;
- a load cell on said bottom swaging die for recording the load to which said bottom swaging die is subjected during a swage event;
- a servomotor coupled with said top swaging die for controlling and recording the location of said top swaging die along the swaging axis, and a control system comprising a microprocessor in communication with said load cell and said servomotor, wherein said microprocessor uses said recorded load to determine the total load applied during a swage event, and wherein said microprocessor uses said recorded location to calculate a total displacement of said top swaging die during the swage event;
- wherein said bottom swaging die comprises: a hinged mechanism including a bottom plate coupled with said frame; a top plate overlying said bottom plate, wherein said top and bottom plates are pivotally connected to one another for enabling said top plate to pivot relative to said bottom plate, and wherein said load cell is disposed between said top and bottom plates; and a swaging tool mounted on said top plate that extends toward said top swaging die along the swaging axis.

14. The programmable swaging press as claimed in claim 13, wherein said top swaging die is mounted on a precision slide that is coupled with said servomotor for controlling one-dimensional, up and down movement of said top swaging die along the swaging axis.

15. The programmable swaging press as claimed in claim 13, further comprising said control system including said microprocessor and having one or more swage programs stored therein for forming armed surgical needles, wherein each said swage program comprises a displacement limit and a load limit for use during a swage event, wherein said displacement limit comprises an upper limit for a total displacement of a needle during the swage event, and wherein said load limit comprises an upper limit for the total load to which said needle can be subjected during the swage event.

16. The programmable swaging press as claimed in claim 15, wherein said microprocessor is in communication with said servomotor for determining the total displacement of said needle during the swage event, and said microprocessor is in communication with said load cell for determining the total load to which said needle is subjected during the swage event.

17. The programmable swaging press as claimed in claim 16, wherein each said program comprises a second displacement limit and a second load limit for use during a second swage event, wherein said second displacement limit is different than said first displacement limit, and wherein said second load limit is different than said first load limit.

18. The programmable swaging press as claimed in claim 16, wherein said microprocessor generates a message that said armed surgical needle is good if the displacement limit has been reached and the load limit has not been exceeded, and wherein said microprocessor generates a message that said armed surgical needle is bad if the load limit has been exceeded.

19. The programmable swaging press as claimed in claim 18, wherein each said swage program further comprises a hit limit during the swage event, wherein said hit limit comprises a total number of times said needle is hit during the swage event.

20. A programmable swaging press for attaching surgical needles to sutures comprising:
- a frame;
- a bottom swaging die mounted on said frame;
- a top swaging die mounted on said frame and being moveable up and down along a swaging axis that is in alignment with said bottom swaging die;
- said bottom swaging die comprising a hinged mechanism including a bottom plate coupled with said frame, a top plate overlying said bottom plate, wherein said top and bottom plates are pivotally connected to one another for enabling said top plate to pivot relative to said bottom plate, a swaging tool mounted on said top plate that extends toward said top swaging die along the swaging axis, a load cell disposed between said top and bottom plates for recording the load to which said bottom swaging die is subjected, a control system comprising a servomotor coupled with said top swaging die for recording location data related to the location of said top swaging die along the swaging axis, and a microprocessor in communication with said load cell for receiving the recorded load and detecting changes in the recorded load, and said microprocessor is in communication with said servomotor for determining the location of said top swaging die along the swaging axis.

21. The programmable swaging press as claimed in claim 20, wherein said top swaging die is mounted on a precision slide that is coupled with said servomotor for controlling one-dimensional, up and down movement of said top swaging die along the swaging axis.

* * * * *